(12) United States Patent
Cole

(10) Patent No.: US 7,252,050 B2
(45) Date of Patent: Aug. 7, 2007

(54) SUBSTANCE INHALATION SYSTEM

(76) Inventor: Maury Dean Cole, 4130 La Jolla Village Dr., MB 107-73, La Jolla, CA (US) 92037

( * ) Notice: Subject to any disclaimer, the term of this patent is extended or adjusted under 35 U.S.C. 154(b) by 711 days.

(21) Appl. No.: 10/656,589

(22) Filed: Sep. 4, 2003

(65) Prior Publication Data

US 2005/0051165 A1 Mar. 10, 2005

(51) Int. Cl.
  *A01K 1/00* (2006.01)
  *A01K 1/03* (2006.01)
  *A61G 10/00* (2006.01)
(52) U.S. Cl. .................. 119/416; 128/205.26; 600/21; 119/417
(58) Field of Classification Search ............... 119/416, 119/417, 418, 419, 420, 421, 441; 600/21; 128/203.12, 203.14, 203.17, 203.26, 203.25, 128/202.16, 205.26, 204.23
See application file for complete search history.

(56) References Cited

U.S. PATENT DOCUMENTS

| | | | | |
|---|---|---|---|---|
| 2,141,794 A | * | 12/1938 | King ..................... | 128/203.19 |
| 3,367,308 A | * | 2/1968 | Quattrone et al. ......... | 119/420 |
| 3,464,388 A | * | 9/1969 | Stout ................... | 119/418 |
| 3,537,428 A | * | 11/1970 | Montgomery ............. | 119/419 |
| 3,838,687 A | * | 10/1974 | Mosher ................. | 128/200.11 |
| 4,348,985 A | * | 9/1982 | Leong .................. | 119/420 |
| 4,520,808 A | * | 6/1985 | LaBauve ............... | 128/200.14 |
| 4,526,133 A | * | 7/1985 | LoMaglio ............... | 119/419 |
| 4,593,650 A | * | 6/1986 | Lattuada ............... | 119/419 |
| 4,690,100 A | * | 9/1987 | Thomas ................ | 119/419 |
| 4,699,088 A | * | 10/1987 | Murray et al. .......... | 119/419 |
| 4,787,382 A | * | 11/1988 | Pekovic ................ | 128/203.25 |
| 4,941,431 A | * | 7/1990 | Anderson et al. ......... | 119/420 |
| 5,379,777 A | * | 1/1995 | Lomask ................ | 600/529 |
| 5,400,744 A | * | 3/1995 | Coiro et al. ............ | 119/72.5 |
| 6,158,434 A | * | 12/2000 | Lugtigheid et al. ....... | 128/204.22 |
| 6,352,076 B1 | * | 3/2002 | French ................ | 128/203.12 |
| 6,776,158 B1 | * | 8/2004 | Anderson et al. ........ | 128/203.12 |
| 2003/0062042 A1 | * | 4/2003 | Wensley et al. ......... | 128/203.12 |

* cited by examiner

*Primary Examiner*—Justine R. Yu
*Assistant Examiner*—Adam Brandt
(74) *Attorney, Agent, or Firm*—Procopio, Cory, Hargreaves & Savitch LLP; Lisel M. Ferguson, Esq.

(57) ABSTRACT

A substance inhalation system includes a mixing flask that is in fluid communication with plural inhalation chambers. A test vapor can be selectively and individually provided to the inhalation chambers. Moreover, individual inhalation chambers can be selectively removed from the substance inhalation system without test vapor leaking from any of the inhalation chambers.

15 Claims, 11 Drawing Sheets

SUBSTANCE INHALATION SYSTEM

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

Not Applicable

BACKGROUND OF THE INVENTION

1. Field of the Invention

This invention pertains generally to substance abuse research systems, and more particularly to substance inhalation systems.

2. Description of Related Art

The destructive effects of alcohol are vast and well known and have led to the creation of the National Institute of Alcohol and Alcohol Abuse (NIAAA) by the Public Health System. Over the years, investigators funded by NIAAA have developed several systems for the delivery of alcohol which include presenting the drug as a liquid diet; injecting alcohol via gastric, intraperitoneal or intravenous routes; and by exposing test subjects, e.g., rodents, to alcohol vapors. Each method has advantages and drawbacks that are abundantly discussed in the available literature. However, one significant problem that has consistently plagued research is the difficulty in reaching predictable blood alcohol levels (BALs) and, if desired, maintain them within given values. Injections of a specific concentration of alcohol can be used but this procedure is very stressful unless the animals are equipped with indwelling permanent cannulae. This requires skillful surgical training. Gavage via the forceful placement of a special tube into the esophagus can be done but is also very stressful, particularly if it is used repeatedly. Also both methods (injections and gavage) induce rapid peak BALs followed by the disappearance of alcohol from the circulation. They cannot be used to maintain constant BALs over time. Feeding alcohol in the diet presents the advantage of voluntary drug intake but does not provide the investigator with significant control over the amount of alcohol consumed, and consequently BALs.

All of these problems have been critical barriers in alcohol research. For this reason, many investigators have turned to delivery of alcohol through vapors. This method, as presently used, allows preparation of animals with more predictable BALs than the diet. However, it has its own inherent technical obstacles. For example, presently available alcohol vapor chambers systems are very large because they can contain up to fifteen test subject cages. These chambers typically require an entire dedicated room and are built "in house", which makes the data collected completely unique to each system. Therefore, it is often difficult to achieve reproducible results from chamber to chamber and from experiment to experiment. Another major obstacle with these systems is that they are built to house many animals together. This requires the investigator to open the entire system to remove one animal, for example to check its BAL. This unavoidably destroys the ethanol-air balance in the system, which requires time to return to equilibrium. Additionally, the handling of the animal causes stress hormones such as corticosterone to be released, which can interfere with the outcome of the results. Finally, not only is the initial cost of building these systems very high, the expense to run them is also high given that they require a full-time employee dedicated to their maintenance.

The present invention recognizes the present drawbacks and provides a solution to one or more of the problems associated therewith.

BRIEF SUMMARY OF THE INVENTION

A substance inhalation system includes a mixing flask that is in fluid communication with a first inhalation chamber and a second inhalation chamber. A test vapor can be selectively and individually provided to the first inhalation chamber and the second inhalation chamber. Additionally, the first inhalation chamber and the second inhalation chamber can be selectively removed from the substance inhalation system without test vapor leaking from either inhalation chambers.

In a preferred embodiment, the system is portable. Specifically, the system a cart having plural wheels attached to the cart. The mixing flask, the first inhalation chamber, and the second inhalation chamber are placed on the cart. Preferably, a heater is thermally coupled to the mixing flask. Also, a test fluid reservoir and an air source are in fluid communication with the mixing flask. Air from the air source is mixed with a test fluid from the test fluid reservoir within the mixing flask.

In a preferred embodiment, a pump is in fluid communication with the test fluid reservoir and the mixing flask. The pump is used to pump test fluid from the test fluid reservoir to the mixing flask. Moreover, a first flow meter/controller in is fluid communication with the mixing flask and the first inhalation chamber and a second flow meter/controller is in fluid communication with the mixing flask and the second inhalation chamber. Preferably, the first flow meter/controller selectively controls the flow of test vapor to the first inhalation chamber and the second flow meter/controller selectively controls the flow of test vapor to the second inhalation chamber.

In another aspect of the present invention, an inhalation chamber lid assembly is provided for enclosing an inhalation chamber. The inhalation chamber lid assembly includes a lid plate and a disconnect fitting installed in the lid plate. The disconnect fitting includes a one-way valve incorporated therein. As such, a fluid line can be disconnected from the disconnect fitting without a test vapor leaking from the disconnect fitting.

In this aspect of the present invention, the inhalation chamber lid assembly includes plural latches attached to the lid plate. The latches securely fasten the inhalation chamber lid assembly to the inhalation chamber. Additionally, a gasket is placed between inhalation chamber lid assembly and the inhalation chamber and seals the inhalation chamber. Further, a rubber plug is removably installed within the lid plate. The rubber plug can removed to provide access to the inhalation chamber.

In this aspect of the present invention, the inhalation chamber lid assembly further includes a thumb screw that is threadably engaged with the lid plate. The thumb screw can be loosened to vent the inhalation chamber. Also, the inhalation chamber lid assembly includes a divider that extends from the lid plate into the inhalation chamber. The divider divides the inhalation chamber into a first portion and a second portion. As such, a test subject can be placed within the first portion of the inhalation chamber and a test subject can be placed within the second portion of the inhalation chamber. The inhalation chamber lid assembly also includes a first water cup and a second water cup attached to a bottom surface of the lid plate. A sipper tube extends each water cup and each water cup is located on an opposite side of the divider.

In yet another aspect of the present invention, a substance inhalation system includes a mixing flask and a test fluid reservoir that is in fluid communication with the mixing flask. A first inhalation chamber and a second inhalation chamber are in fluid communication with the mixing flask. A flow meter/controller is in fluid communication with the mixing flask and each inhalation chamber. A microprocessor electrically connected to the flow meter/controllers. The microprocessor includes logic for selectively and individually controlling the flow of test vapor to the first inhalation chamber and the second inhalation chamber.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 11. It will be appreciated that the apparatus may vary as to configuration and as to details of the parts, and that the method may vary as to the specific steps and sequence, without departing from the basic concepts as disclosed herein.

Description of a Preferred Embodiment of the Present Invention

Figure 1:
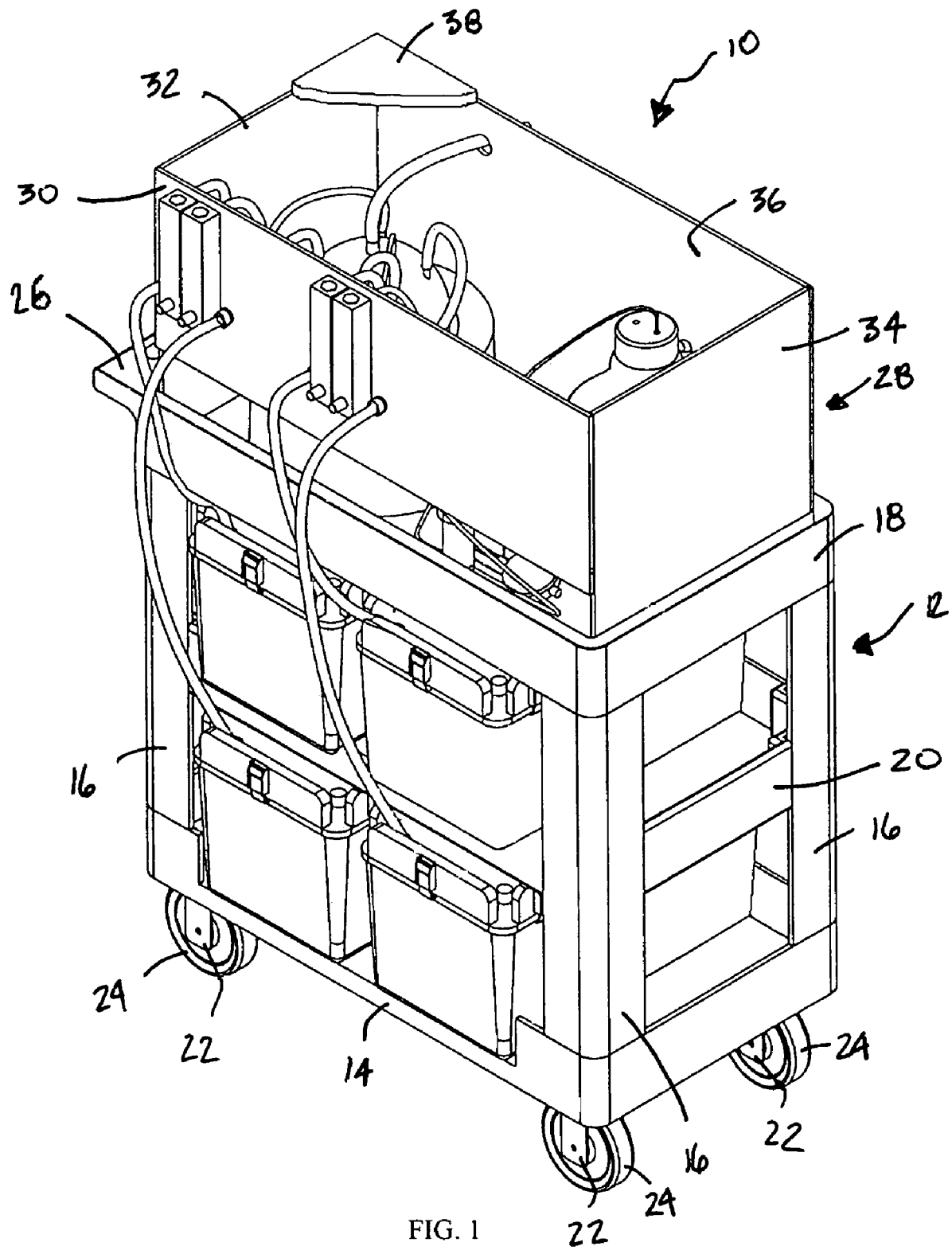
FIG. 1 is a perspective view of a substance inhalation system according to the present invention with a lid partially cut away to reveal the components covered thereby.
Figure 2:
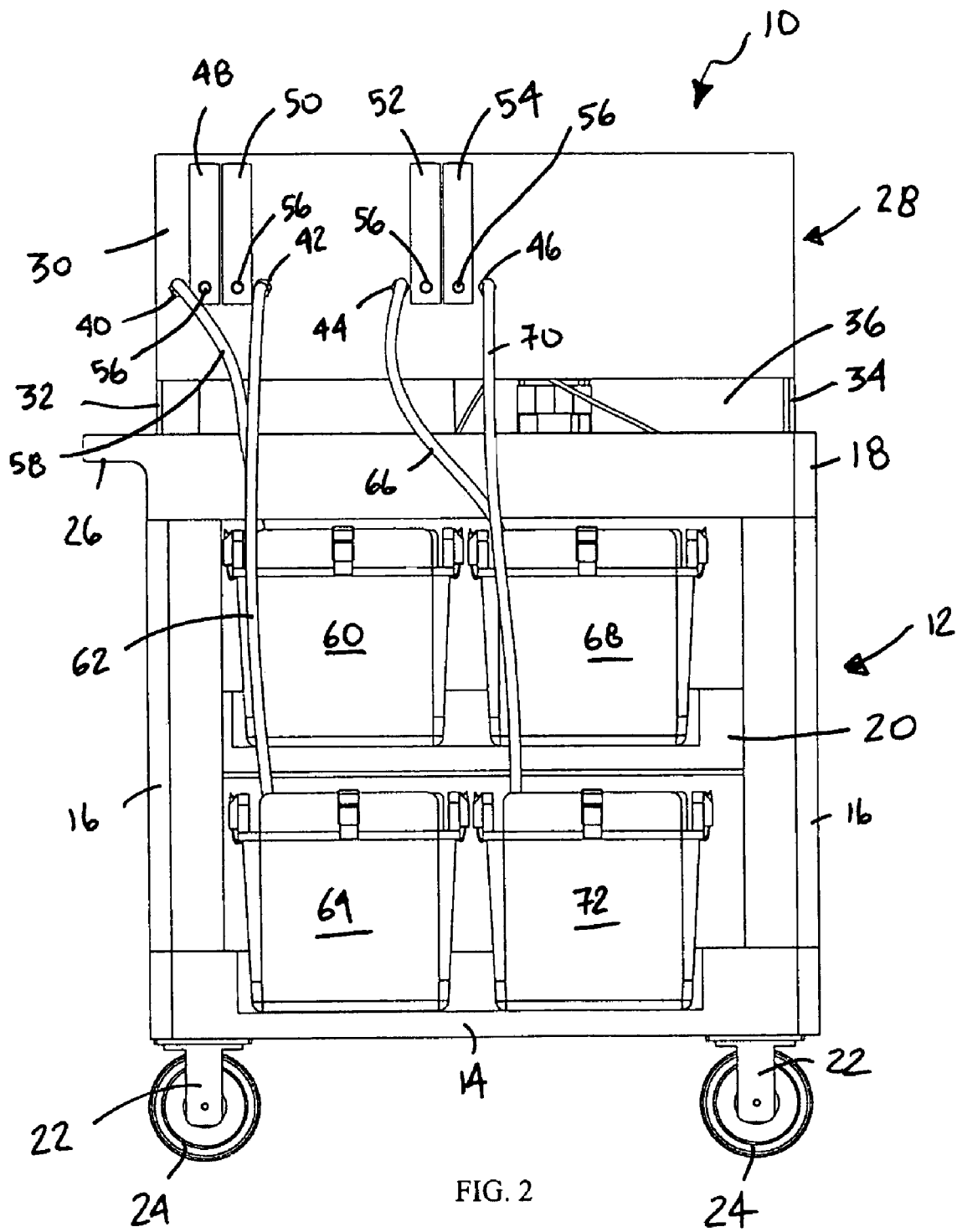
FIG. 2 is a front plan view of the substance inhalation system according to the present invention.

Referring initially to FIG. 1 and FIG. 2, a substance inhalation system is shown and is generally designated 10. As shown, the substance inhalation system 10 includes a cart 12 having a generally rectangular bottom shelf 14. Four legs 16 extend perpendicularly from the bottom shelf 14 and provide support for a top shelf 18. FIG. 1 and FIG. 2 further shows a middle shelf 20 installed between the bottom shelf 14 and the top shelf 18. Additionally, four wheel mount brackets 22 are attached to the bottom shelf 14. Each wheel mount bracket 22 supports a wheel 24. It can be appreciated that the cart 12 can be rolled on the wheels 24 for transport, positioning, etc. A handle 26 extends from the top shelf 18 and can be used for pushing and/or pulling the cart 12.

FIG. 1 and FIG. 2 also show a housing 28 that extends from the top shelf 18. As shown, the housing 28 includes a front cover 30, a left side cover 32, a right side cover 34, and a back cover 36. Moreover, as shown in FIG. 1, a lid 38 can be installed on the housing 28 to protect the components disposed within the housing 28.

Referring now to FIG. 2 only, a first hose fitting 40, a second hose fitting 42, a third hose fitting 44, and a fourth hose fitting 46 are mounted in the front cover 30 of the housing 28. Preferably, the hose fittings 40, 42, 44, 46 are barb fittings. FIG. 2 also shows a first flow meter/controller 48, a second flow meter/controller 50, a third flow meter/controller 52, and a fourth flow meter/controller 54 that are also mounted in the front cover 30 of the housing 28. Preferably, the flow meters 48, 50, 52, 54 can be Visi-Float® flow meters manufactured by Dwyer®. Each flow meter/controller 48, 50, 52, 54 is mounted next to a respective hose fitting 40, 42, 44, 46. Moreover, each flow meter/controller 48, 50, 52, 54 includes a knob 56 for adjusting the flow therethrough.

Referring again to both FIG. 1 and FIG. 2, a first lower vapor delivery line 58 is shown and is connected between the first hose fitting 40 and a first inhalation chamber 60. A second lower vapor delivery line 62 is connected between the second hose fitting 42 and a second inhalation chamber 64. Moreover, a third lower vapor delivery line 66 is connected between the third hose fitting 44 and a third inhalation chamber 68. And, a fourth lower vapor delivery line 70 is connected between the fourth hose fitting 46 and a fourth inhalation chamber 72. As shown in FIG. 1 and FIG. 2, the second and fourth inhalation chambers 64, 72 are placed on the bottom shelf 14 of the cart. Also, the first and third inhalation chambers 60, 68 are placed on the middle shelf 20 of the cart 12. It is to be understood that each of the inhalation chambers 60, 64, 68, 72 are identical and each includes a inhalation chamber lid assembly, described in detail below. Further, it can be appreciated that the system can include more than or less than four inhalation chambers 60, 64, 68, 72 depending on a particular user's research needs.

Figure 3:
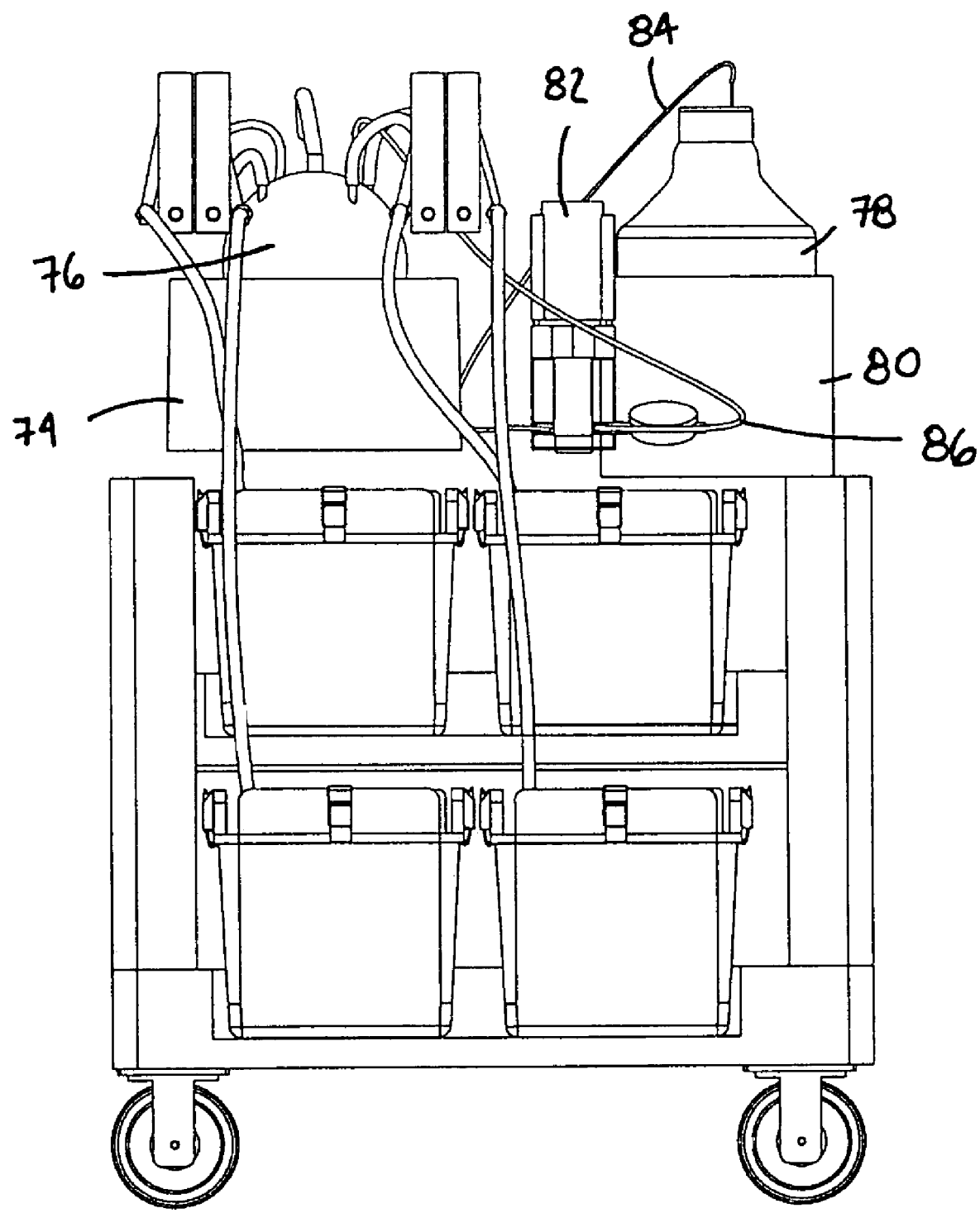
FIG. 3 is a front plan view of the substance inhalation system according to the present invention with a top shelf and a housing removed to reveal the components therein.
Figure 4:
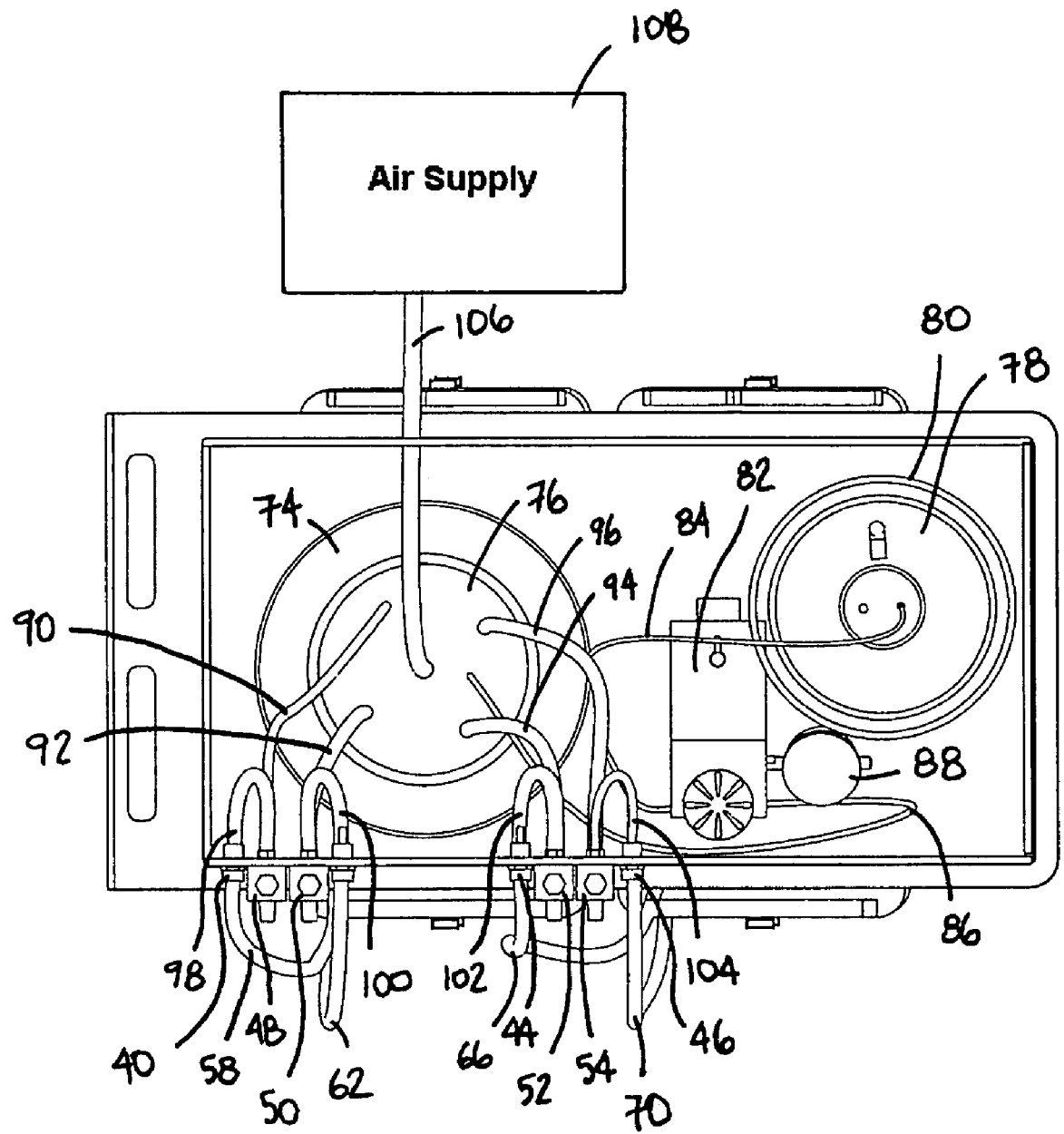
FIG. 4 is a top plan view of the substance inhalation system according to the present invention with a lid removed to reveal the components covered thereby.

Referring now to FIG. 3 and FIG. 4, details concerning the components of the substance inhalation system 10 located within the housing 28 can be seen. As shown in FIG. 3 and FIG. 4, the substance inhalation system 10 further includes a heater 74 in which a mixing flask 76 is partially disposed so that it is thermally coupled to the heater 74 to allow heat exchange from the heater 74. The mixing flask 76 is described in detail below. FIG. 3 and FIG. 4 also show a test fluid reservoir 78 at least partially disposed within a reservoir ring 80. As shown, the test fluid reservoir 78 is connected to a test fluid pump 82 via a first test fluid line 84. In turn, the pump 82 is connected to the mixing flask 76 via a second test fluid line 86. The pump 82 includes a dial indicator 88 that can be used to indicate the displacement of the pump 82. It is to be understood that the pump 82 can be used to pump a test fluid from the test fluid reservoir 78 to the mixing flask 76. It can be appreciated that the test fluid can be ethanol alcohol or any other liquid, solution, etc.

Referring to FIG. 4 only, it is shown that the mixing flask 76 is connected to the first flow meter/controller 48 by a first upper vapor delivery line 90. The mixing flask 76 is also connected to the second flow meter/controller 50 via a second upper vapor delivery line 92. Moreover, the mixing flask 76 is connected to the third flow meter/controller 52 via a third upper vapor delivery line 94. And, the mixing flask 76 is connected to the fourth flow meter/controller 54 via a fourth upper vapor delivery line 96. As such, the mixing flask 76 is in fluid communication with each flow meter/controller 48, 50, 52, 54 via the upper vapor delivery lines 90, 92, 94, 96.

FIG. 4 further shows that the first flow meter/controller 48 is connected to the first hose fitting 40 via a first intermediate vapor delivery line 98 and is fluid communication with the first hose fitting 40. The second flow meter/controller 50 is in fluid communication with the second hose fitting 42 via a second intermediate vapor delivery line 100. Also, the third flow meter/controller 52 is in fluid communication with the third hose fitting 44 via a third intermediate vapor delivery line 102. And, the fourth flow meter/controller 54 is in fluid communication with the fourth hose fitting 46 via a fourth intermediate vapor deliver line 104. Accordingly, the mixing flask 76 can be in fluid communication with each inhalation chamber 60, 64, 68, 72 via an upper vapor delivery line 90, 92, 94, 96, a flow meter/controller 48, 50, 52, 54, an intermediate vapor delivery line 98, 100, 102, 104, and a lower vapor delivery line 58, 62, 66, 70.

FIG. 4 also shows an air intake line 106. It can be appreciated that the air received within the mixing flask 76 via the air intake line 106 can be ambient air. In the alternative, the air intake line 106 can be connected to an air supply 108, e.g., an air tank, a valve from a laboratory air source, etc.

Description of a Preferred Mixing Flask

Figure 5:
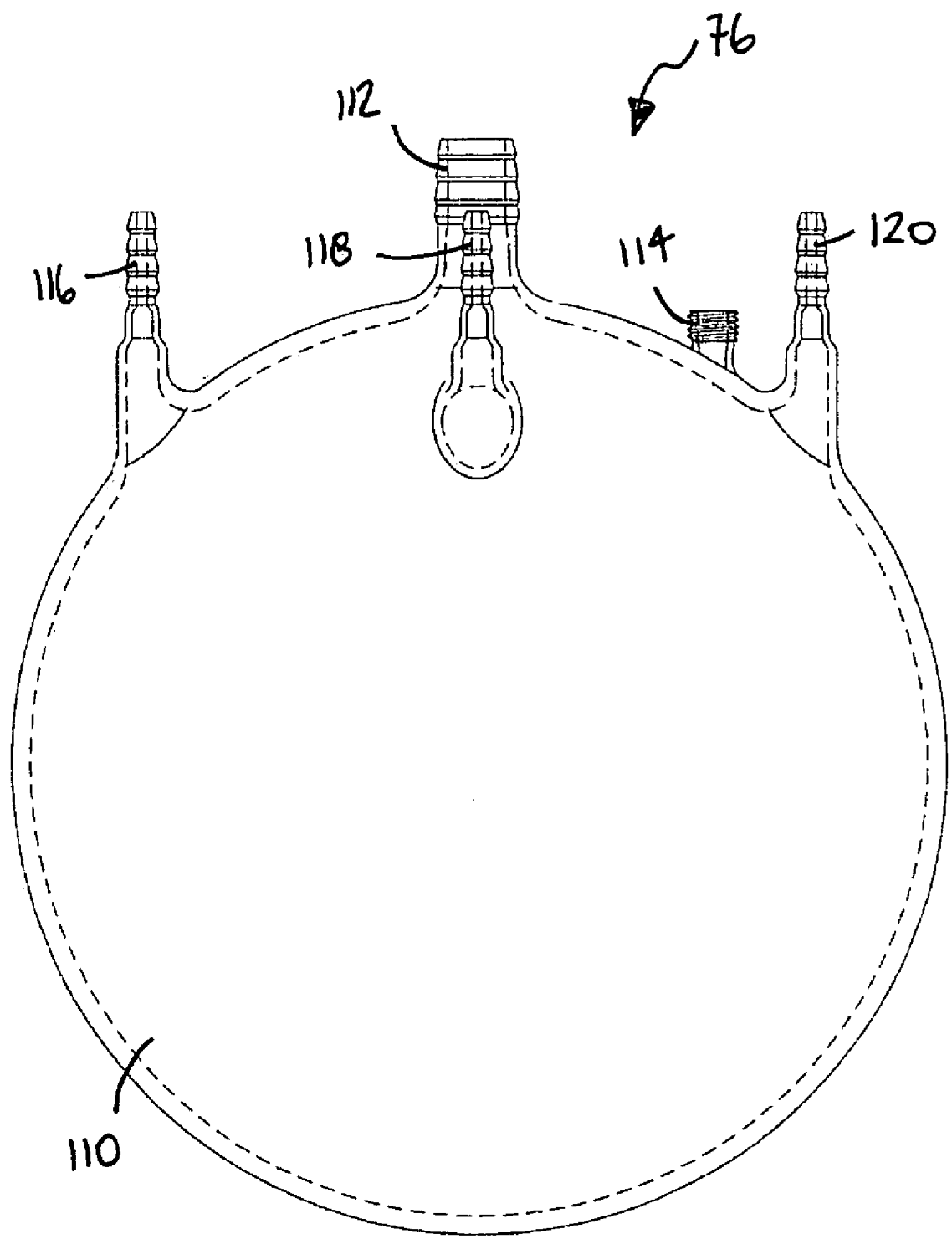
FIG. 5 is a side plan view of a mixing flask according to the present invention.
Figure 6:
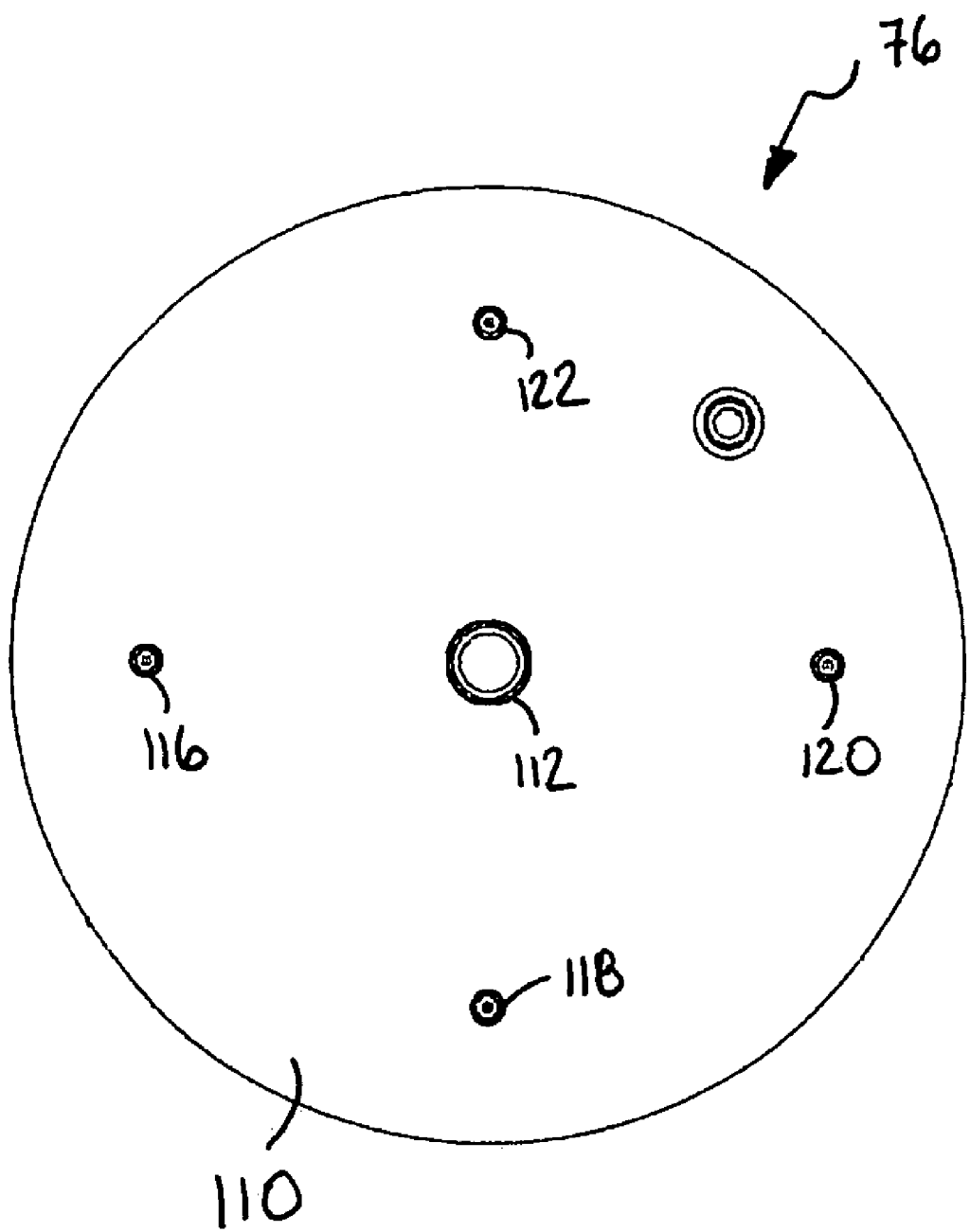
FIG. 6 is a top plan view of the mixing flask according to the present invention.

Referring now to FIG. 5 and FIG. 6, details concerning the construction of the mixing flask 76 are shown. As shown in FIG. 5 and FIG. 6, the mixing flask 76 has a generally spherical body 110 from which an air inlet 112 extends in a generally upward direction from the top of the spherical body 110. Moreover, a test fluid inlet 114 extends from the top of the mixing flask 76 in the same direction as the air inlet 112. Additionally, a first vapor outlet 116, a second vapor outlet 118, a third vapor outlet 120, and a fourth vapor outlet 122 extend from the top of the mixing flask 76 in the same direction as the air inlet 112 and the test fluid inlet 114.

It can be appreciated that the air intake line 106 is connected to the air inlet 112 formed in the mixing flask 76. Further, the second test fluid line 86 is connected to the test fluid inlet 114. Also, each upper vapor delivery line 90, 92, 94, 96 is connected to a respective vapor outlet 116, 118, 120, 122. Accordingly, as intended by the present invention, air and test fluid can be provided to the mixing flask 76 via the air inlet 112 and the test fluid inlet 114. The mixing flask 76 can be heated by the heater 74 to create a test fluid vapor. In turn, the test fluid vapor can be provided to one or more of the inhalation chambers 60, 64, 68, 72 via the vapor outlets 116, 118, 120, 122.

Description of a Preferred Inhalation Chamber Lid Assembly

Figure 7:
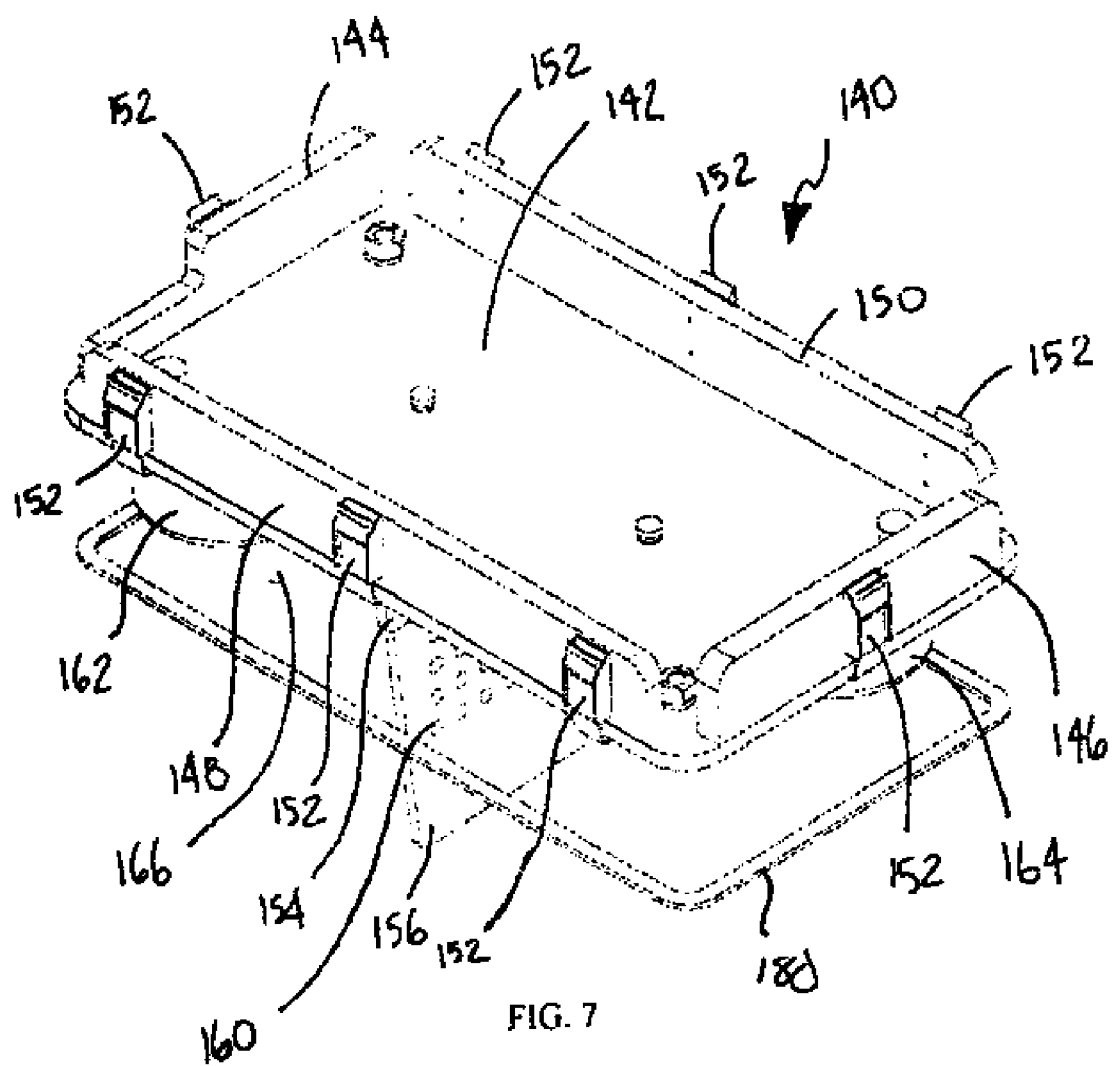
FIG. 7 is a perspective view of an inhalation chamber lid assembly according to the present invention.
Figure 8:
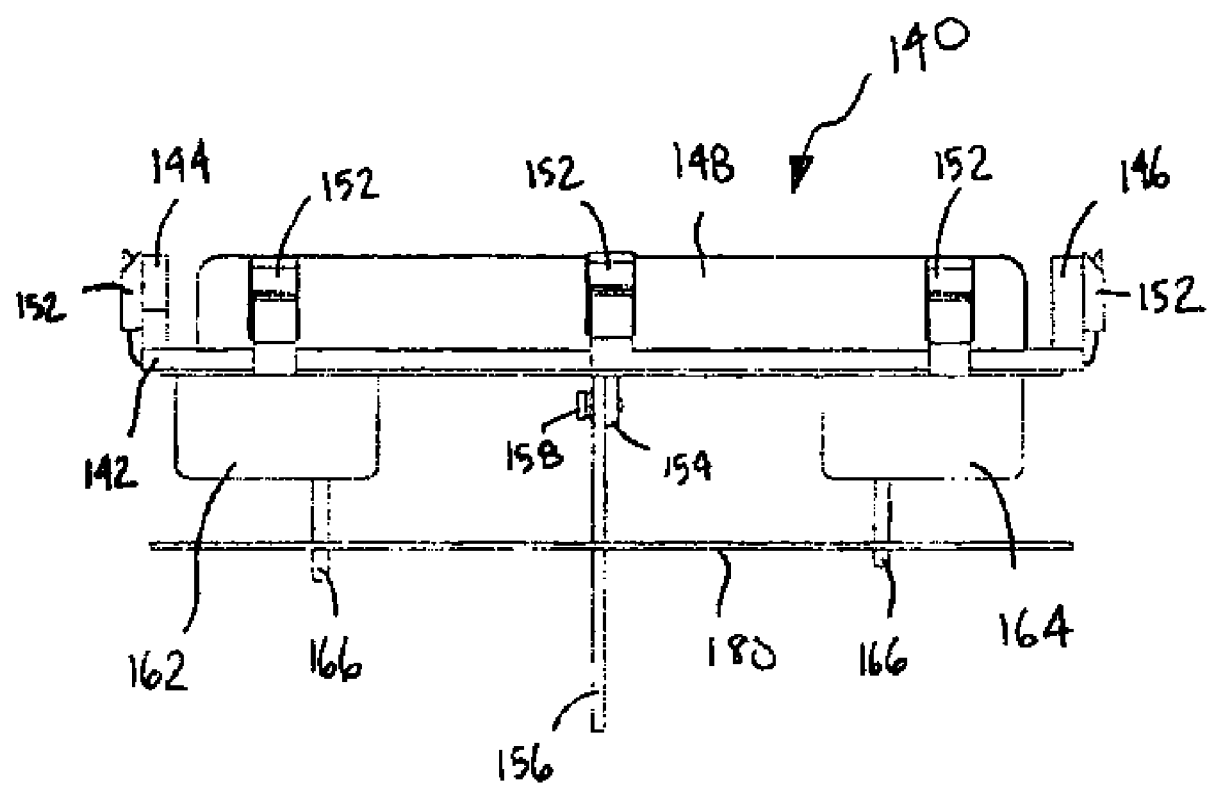
FIG. 8 is a side plan view of the inhalation chamber lid assembly according to the present invention.
Figure 9:
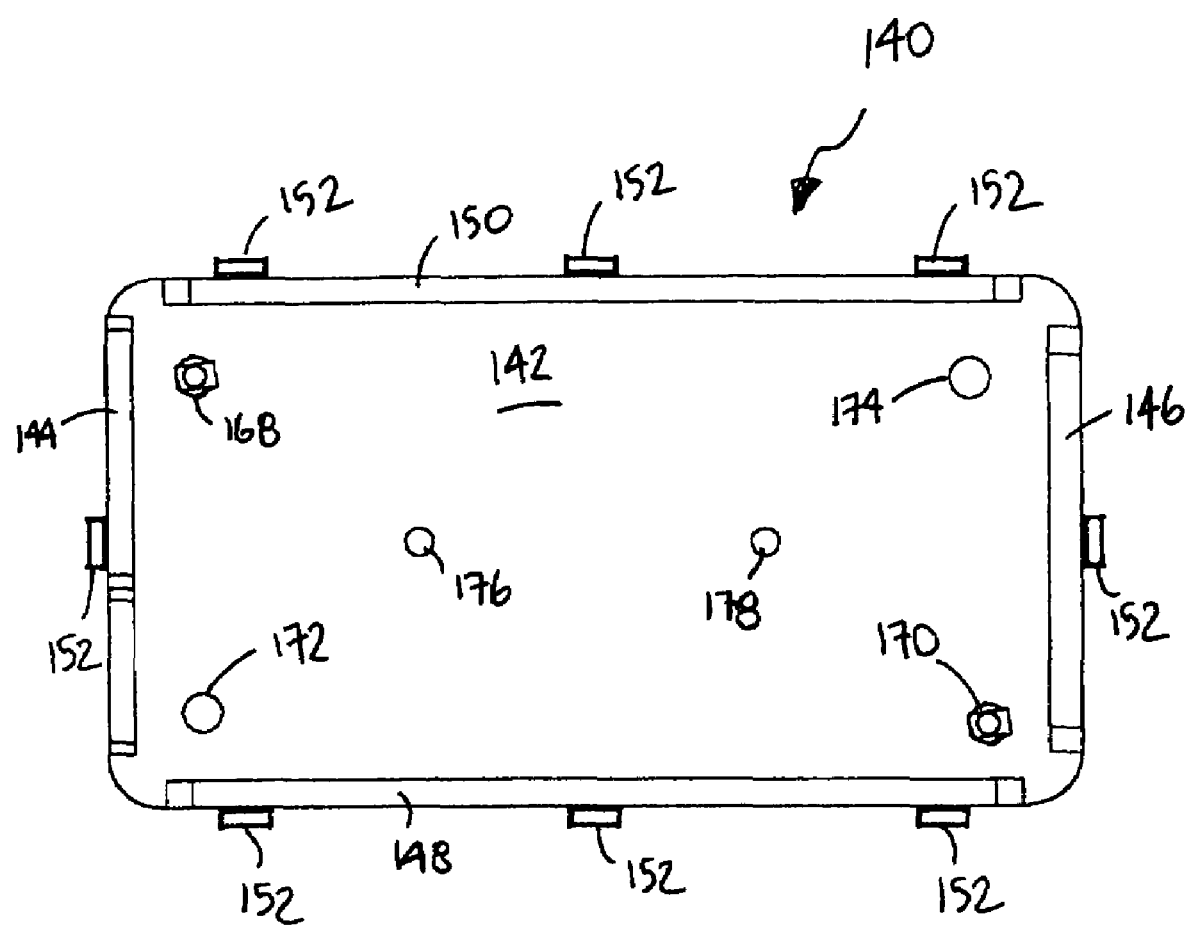
FIG. 9 is a top plan view of the inhalation chamber lid assembly according to the present invention.

Referring to FIG. 7 through FIG. 9, an inhalation chamber lid assembly is shown and is generally designated 140. As shown, the inhalation chamber lid assembly 140 includes a generally rectangular lid plate 142. A left side rail 144 extends perpendicularly from the top of the lid plate 142 adjacent to the left edge of the lid plate 142. A right side rail 146 extends perpendicularly from the top of the lid plate 142 adjacent to the right edge of the lid plate 142, i.e., parallel to and opposite of the left side rail 144.

Further, as shown in FIG. 7 through FIG. 9, a front rail 148 extends from the top of the lid plate 142 adjacent to the front edge of the lid plate 142, i.e., perpendicular to the left side rail 144 and the right side rail 146. A rear rail 150 extends from the top of the lid plate 142 adjacent to the rear edge of the lid plate 142, i.e., parallel to and opposite of the front rail 148. FIG. 7 through FIG. 9 also show at least one latch 152, e.g., a latch manufactured by SOUTHCO®, that is attached to each rail 144, 146, 148, 150. Preferably, one latch 152 is attached to the left rail 144 and one latch 152 is attached to the right rail 146. Moreover, in a preferred embodiment, three latches 152 are attached to the front rail 148 and three latches 152 we attached do the rear rail 150. It is to be understood that the latches 152 can be used to securely fasten the inhalation chamber lid assembly 140 to an inhalation chamber 60, 64, 68, 72 (shown in FIG. 1 through FIG. 3). In a preferred embodiment, each inhalation chamber can be a clear plastic, rodent cage manufactured by Allentown Caging Equipment.

FIG. 7 and FIG. 8 also show that the inhalation chamber lid assembly 140 further includes a divider mount 154 that extends in a generally downward direction from the lid plate 142. As shown, a generally rectangular, preferably clear plastic divider 156 is attached to the divider mount 154 by one or more fasteners 158. In a preferred embodiment, the divider 156 can be formed with plural holes 160 to allow air/vapor to pass therethrough. It can be appreciated that the divider 156 divides the inhalation chamber 60, 64, 68, 72 divides the inhalation chamber 60, 64, 68, 72 into a first portion and a second portion into which test subjects can be placed during inhalation and testing.

As further shown in FIG. 7 and FIG. 8, a first water cup 162 and a second water cup 164 are attached to the bottom of the lid plate, e.g., one water cup 162, 164 on each side of the divider 156. It is to be understood that each water cup 162, 164 is generally cylindrical in shape and includes a sipper tube 166 that extends in a generally downward direction from the water cup 162. Accordingly, as intended by the present invention, test subjects, e.g., rodents, can be placed in the inhalation chambers 60, 64, 68, 72 on separate sides of the divider 156. Food can be placed on with the inhalation chambers 60, 64, 68, 72 on each side of the divider 156 and water can be supplied to the test subjects via the water cups 162, 166 and the sipper tubes 166.

FIG. 9 shows that the inhalation chamber lid assembly 140 further includes a first disconnect fitting 168 and a second disconnect fitting 170 that are installed in the lid plate 142 such that one disconnect fitting 168, 170 provides fluid communication to each side of the divider 156 (FIG. 7 and FIG. 8). It is to be understood that a fluid line, e.g., a lower vapor delivery line 58, 62, 66, 70 (FIG. 1 through FIG. 4), can be attached to either of the disconnect fittings 168, 170. It is to be further understood that each disconnect fitting 168, 170 includes a one-way valve to prevent vapor from escaping the inhalation chamber 60, 64, 68, 72 when a lower vapor delivery line 58, 62, 66, 70 is removed from the disconnect fitting 168, 170. Accordingly, as intended by the present invention, when a predetermined amount of vapor can be provided to the inhalation chamber 60, 64, 68, 72, the lower vapor delivery line 58, 62, 66, 70 can be removed from the inhalation chamber 60, 64, 68, 72 and the inhalation chamber 60, 64, 68, 72 can be removed from the substance inhalation system 10. Then, a vapor free inhalation chamber can be placed in the substance inhalation system 10 and the vapor free inhalation chamber can be dosed with a new amount of test vapor. Accordingly, test subjects can be removed from an individual inhalation chamber 60, 64, 68, 72 without disturbing the test subjects or the vapor density in the other inhalation chambers 60, 64, 68, 72.

Moreover, a preferably rubber first plug 172 and a preferably rubber second plug 174 can be removably engaged with the lid plate 142. These plugs 172, 174, when removed, provide an access port to the interior of the inhalation chamber 60, 64, 68, 72 (FIG. 1 through FIG. 3), on each side of the divider 156 (FIG. 7 and FIG. 8), through which a probe, wire, catheter, etc., can extend. After the probe, wire, catheter, etc., is installed through the lid plate 142, the plugs 172, 174 can be replaced to seal the lid plate 142.

As intended by the present invention, for example, a probed test subject can be placed in the inhalation chamber 60, 64, 68, 72 (FIG. 1 through FIG. 3) and monitored during the test fluid vapor inhalation process. As further shown in FIG. 9, a first thumb screw 176 and a second thumb screw 178 are threadably engaged with the lid plate 142 on each side of the divider 156. It can be appreciated that the thumb screws 176, 178 can be loosened and/or removed to vent the inhalation chamber 60, 64, 68, 72 (FIG. 1 through FIG. 3) prior to removing inhalation chamber lid assembly 140.

Referring briefly back to FIG. 7 and FIG. 8, a preferably rubber gasket 180 is shown. It can be appreciated that the gasket can be disposed between the lid plate 142 and an upper rim of an inhalation chamber 60, 64, 68, 72 (FIG. 1 through FIG. 3) to effectively seal the inhalation chamber 60, 64, 68, 72 (FIG. 1 through FIG. 3) when the latches 152 are properly engaged with the inhalation chamber 60, 64, 68, 72 (FIG. 1 through FIG. 3) and closed.

Description of a Preferred Control System

Figure 10:
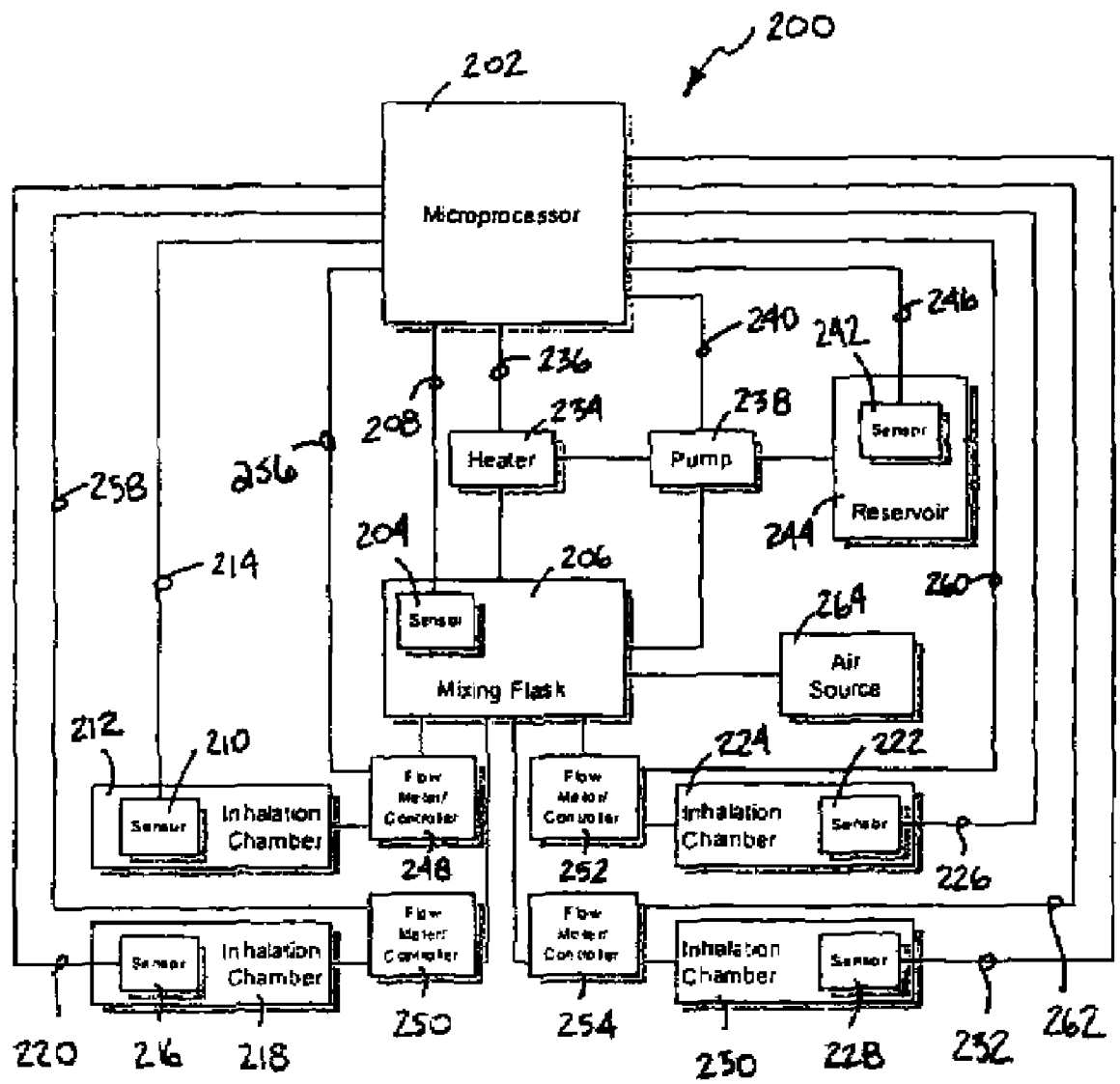
FIG. 10 is a block diagram of a control system according to the present invention.

Referring now to FIG. 10, a control system is shown and is designated 200. As shown, the control system 200 includes a microprocessor 202 that is connected to a temperature sensor 204 within a mixing flask 206 via electrical line 208. Moreover, the microprocessor 202 is connected to a first test parameter sensor 210 within a first inhalation chamber 212 via electrical line 214. The microprocessor 202 is also connected to a second test parameter sensor 216 within a second inhalation chamber 218 via electrical line 220. Further, the microprocessor 202 is connected to a third test parameter sensor 222 within a third inhalation chamber 224 via electrical line 226. And, the microprocessor 202 is also connected to a fourth test parameter sensor 228 within a fourth inhalation chamber 230 via electrical line 232.

As further shown in FIG. 10, the control system 200 includes a heater 234 that is electrically connected to the microprocessor 202 via electrical line 236. Moreover, a pump 238 is electrically connected to the microprocessor 202 via electrical line 240. A level sensor 242 within a test fluid reservoir 244 is connected to the microprocessor 202 via electrical line 246. It is to be understood that the mixing flask 206 is thermally connected to the heater 234. Moreover, the mixing flask 206 is connected to each of the inhalation chambers 212, 218, 224, 230 via a respective first, second, third and fourth flow meter/controller 248, 250, 252, 254. The first flow meter/controller 248 is electrically connected to the microprocessor via electrical line 256. The second flow meter/controller 250 is electrically connected to the microprocessor via electrical line 258. Further, the third flow meter/controller 252 is electrically connected to the microprocessor via electrical line 260. And, the fourth flow meter/controller 254 is electrically connected to the microprocessor via electrical line 262. FIG. 10 also shows an air source 264 that is in fluid communication with the mixing flask 206.

As described in detail below and as intended by the present invention, the microprocessor can control the vaporization of a test fluid within the mixing flask by altering the temperature therein. Moreover, the microprocessor 202 can control the flow of test vapors to the inhalation chambers 212, 218, 224, 230 by controlling the flow meters/controllers 248, 250, 252, 254.

Figure 11:
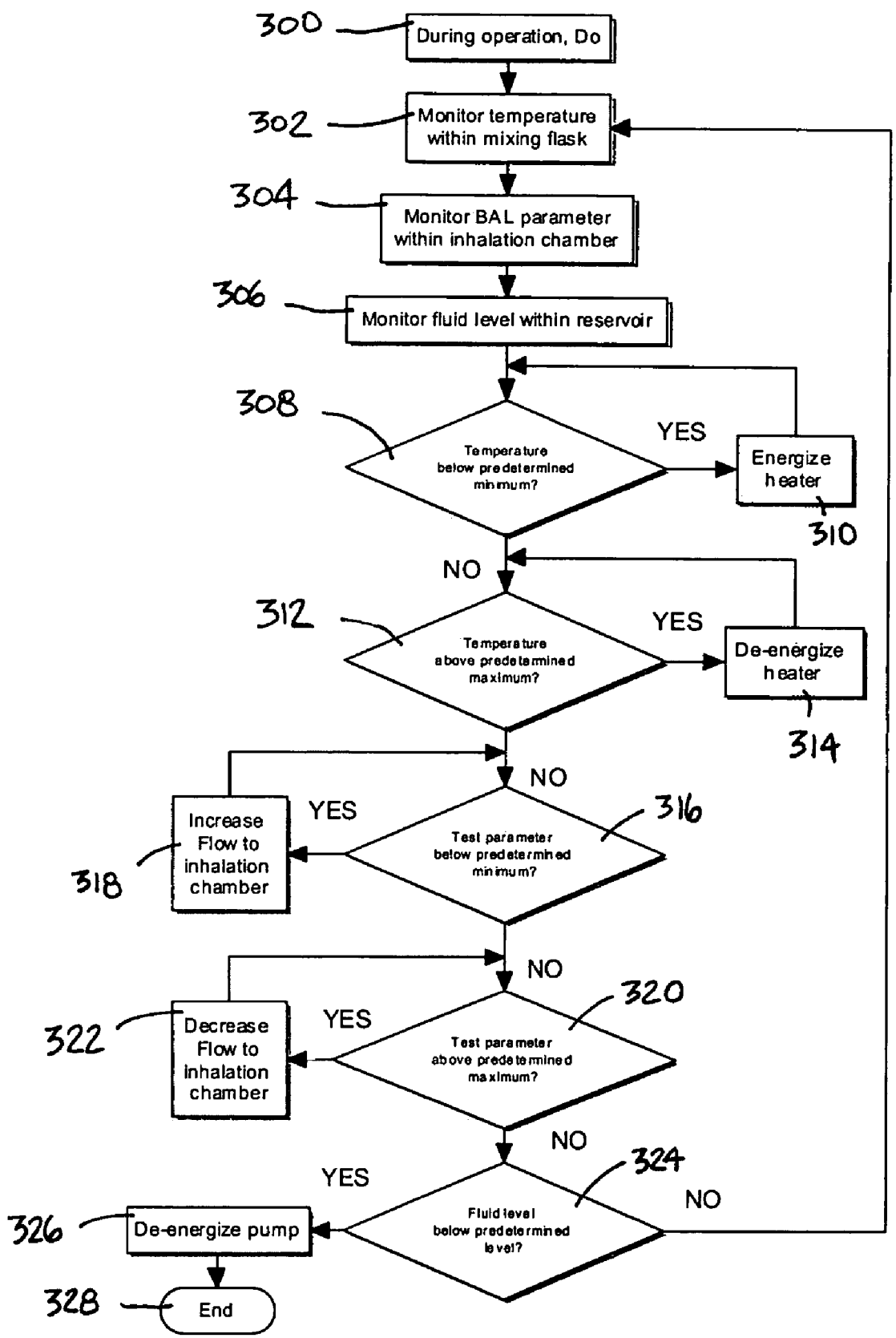
FIG. 11 is a flow chart of an embodiment of the overall operating logic according to the present invention.

Description of a Non-Limiting, Exemplary
Embodiment of the Control Logic Used by the
Control System Referring to FIG. 11, a non-limiting, exemplary embodiment of the overall operating logic according to the present invention is shown and commences at block 300 with a do loop wherein the following steps are performed. At block 302, the temperature is monitored within the mixing flask 206. The temperature within the mixing flask 206 can be monitored using the temperature sensor 204 within, or otherwise in contact with, the mixing flask 206. Moving to block 304, a test parameter within each of the inhalation chambers 212, 218, 224, 230. It can be appreciated that the test parameter can be a BAL parameter that can be monitored by taking blood samples from test subjects within the inhalation chambers 212, 218, 224, 230. In the alternative, the BAL parameter can be a vapor measurement parameter, e.g., a humidity parameter, measured within each inhalation chamber 212, 218, 224, 230. It can be appreciated that the manner in which the BAL parameter relates to the BAL of the test subjects can be determined empirically, i.e., by experimentation, for many test subjects of varying sizes and weights.

Continuing the description of the logic, at block 306, the fluid level is monitored within the reservoir 244, e.g., via the level sensor 242 placed therein. Proceeding to decision diamond 308, it is determined whether the temperature within the mixing flask 206 is below a predetermined minimum. If so, the logic moves to block 310 and the heater 234 is energized. Then, the logic returns to decision diamond 308 and continues as described above.

Otherwise, if the temperature is above the predetermined minimum, the logic continues to decision diamond 312 where it is determined whether the temperature within the mixing flask 206 is above a predetermined maximum. If so, the logic proceeds to block 314 and the heater 234 is de-energized. Thereafter, the logic returns to decision diamond 312 and continues as described above. On the other hand, if the temperature is below the predetermined maximum at decision diamond 312, the logic continues to decision diamond 316 where it is determined whether a test parameter within a particular inhalation chamber 212, 218, 224, 230 is below a predetermined minimum. If so, the logic moves to block 318 and the flow to that particular inhalation chamber 212, 218, 224, 230 is increased. The logic then returns to decision diamond 316 and continues as described above.

If the test parameter is above a predetermined minimum, the logic proceeds to decision diamond 320 where it is determined whether the test parameter is above a predetermined maximum. If so, the logic moves to block 322 and the flow to that particular inhalation chamber 212, 218, 224, 230 is decreased.

Otherwise, if the test parameter is below a predetermined maximum, the logic moves to decision diamond 324. At decision diamond 324, it is determined whether the fluid level within the test fluid reservoir 244 is below a predetermined level. If so, the logic moves to block 326 and the pump 238 is de-energized. Thereafter, the logic ends at state 328. At decision diamond 324, if the fluid level is above a predetermined level, the logic returns to block 302 and continues as described above.

With the configuration of structure described above, it can be appreciated that the substance inhalation system 10 can be used to provide test vapors to multiple subjects in separate inhalation chambers 60, 64, 68, 72. One or more inhalation chambers 60, 64, 68, 72 can be removed from the system without disturbing the remaining inhalation chambers 60, 64, 68, 72. Moreover, the flow of test vapor to the inhalation chambers 60, 64, 68, 72 can be precisely and individually controlled.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. A portable substance inhalation system comprising:
   a mixing flask;
   at least a first inhalation chamber in fluid communication with the mixing flask;
   at least a second inhalation chamber in fluid communication with the mixing flask;
   a cart with a plural of wheels attached;
   a heater thermally coupled to the mixing flask;
   at least one test fluid reservoir in fluid communication with the mixing flask;
   at least one air source in fluid communication with the mixing flask;
   a pump in fluid communication with the test fluid reservoir and the mixing flask;
   wherein a test vapor can be selectively and individually provided to the first inhalation chamber and the second inhalation chamber; and
   wherein the first inhalation chamber and the second inhalation chamber can be selectively removed from the substance inhalation system without test vapor leaking therefrom;
   wherein air from the air source is mixed with a test fluid from the test fluid reservoir within the mixing flask;
   wherein the pump is used to pump test fluid from the test fluid reservoir to the mixing flask; and
   wherein the mixing flask, the first inhalation chamber, and the second inhalation chamber are placed on the cart.

2. A system as in claim 1, further comprising:
   at least a first flow meter/controller in fluid communication with the mixing flask and the first inhalation chamber;
   at least a second flow meter/controller in fluid communication with the mixing flask and the second inhalation chamber;
   wherein the first flow meter/controller selectively controls the flow of vapor to the first inhalation chamber; and
   wherein the second flow meter/controller selectively controls the flow of test vapor to the second inhalation chamber.

3. A system as in claim 1, further comprising:
   a first inhalation chamber lid assembly enclosing the first inhalation chamber; and
   a second inhalation chamber lid assembly enclosing the second inhalation chamber.

4. A system as in claim 3, wherein each inhalation chamber lid assembly comprises:
   a lid plate; and
   at least one disconnected fitting installed in the lid plate;
   wherein the disconnect fitting includes a one-way valve incorporated therein;
   wherein a fluid line can be disconnected from the disconnect filling without test vapor leaking from the disconnect fitting.

5. A system as in claim 4, wherein each inhalation chamber lid assembly further comprises:
   at least one latch attached to the lid plate;
   wherein the latch securely fastens the inhalation chamber lid assembly to the inhalation chamber.

6. A system as in claim 5, wherein each inhalation chamber lid assembly further comprises:
   a gasket placed between the inhalation chamber lid assembly and the inhalation chamber;
   wherein the gasket seals the inhalation chamber.

7. A system as in claim 6, wherein each inhalation chamber lid assembly further comprises:
   at least on rubber plug removably installed with the lid plate;
   wherein the rubber plug is removable to provide access port to the inhalation chamber.

8. A system as in claim 7, wherein each inhalation chamber lid assembly further comprises:
   at least on thumb screw threadably engaged with the lid plate;

wherein the thumb screw can be loosened to vent the inhalation chamber.

9. A system as in claim 8, wherein each inhalation chamber lid assembly further comprises:
at least one divider extending from the lid plate into the inhalation chamber;
wherein the divider divides the inhalation chamber into at least a first portion and at least a second portion; and
wherein at least one test subject can be placed within the first portion of the inhalation chamber and at least one test subject can be placed within the second portion of the inhalation chamber.

10. A system as in claim 9, wherein each inhalation chamber lid assembly further comprises:
at least a first water cup attached to a bottom surface on the lid plate;
at least a second water cup attached to the bottom surface of the lid plate;
at least one sipper tube extending from the first water cup;
at least one sipper tube extending from the second water cup; and
wherein each water cup is located on an opposite side of the divider.

11. An inhalation chamber lid assembly for enclosing an inhalation chamber, the inhalation chamber lid assembly comprising:
a lid plate;
at least one disconnect fitting installed in the lid plate;
at least one latch attached to the lid plate;
a gasket placed between the lid plate and the inhalation chamber;
at least one rubber plug removably installed within the lid plate;
at least one thumb screw threadably engaged with the lid plate;
wherein the disconnect fitting includes a one-way valve incorporated therein;
wherein a fluid line can be disconnected from the disconnect fitting without a test vapor leaking;
wherein the latch securely fastens the inhalation chamber lid assembly to the inhalation chamber;
wherein the gasket seals the inhalation chamber;
wherein the rubber plug is removable to provide access to the inhalation chamber; and
wherein the thumb screw can be loosened to vent the inhalation chamber.

12. An inhalation chamber lid assembly as in claim 11, further comprising:
at least one divider extending from the lid plate into the inhalation chamber;
wherein the divider divides the inhalation chamber into at least a first portion and at least a second portion; and
wherein at least one test subject can be placed within the first portion of the inhalation chamber and at least one test subject can be placed within the second portion of the inhalation chamber.

13. A inhalation chamber lid assembly as in claim 12, further comprising:
at least a first water cup attached to a bottom surface of the lid plate;
at least a second water cup attached the bottom surface of the lid plate;
at least one sipper tube extending from the first water cup;
at least one sipper tube extending from the second water cup; and
wherein each water cup is located on an opposite side of the divider.

14. A substance inhalation system comprising:
a mixing flask;
a test fluid reservoir in fluid communication with the mixing flask;
at least a first inhalation chamber in fluid communication with the mixing flask;
at least a second inhalation chamber in fluid communication with the mixing flask;
at least a first flow meter/controller in fluid communication with the mixing flask and the first inhalation chamber;
at least a second flow meter/controller in fluid communication with the mixing flask and the second inhalation chamber;
a heater thermally coupled to the mixing flask;
a temperature sensor thermally coupled to the mixing flask; and
a microprocessor electronically connected to the first flow meter/controller and the second flow meter/controller, the microprocessor including logic for
selectively and individually controlling the flow of test vapor to the first inhalation chamber and the second inhalation chamber,
determining whether a test parameter is within a predetermined range; and
at least partially based thereon, altering the flow of test vapors to the first inhalation chamber or the second inhalation chamber, and
determining whether a temperature within the mixing flask is within a predetermined operating range, and at least partially based thereon, adjusting the heater.

15. A substance inhalation system as in claim 14, further comprising:
a fluid level sensor disposed with a test fluid reservoir;
a pump in fluid communication with the test fluid reservoir and the mixing flask; and
wherein the microprocessor further comprises logic for:
determining a level of test fluid within the test fluid reservoir; and
at least partially based thereon, selectively de-energizing a pump.

* * * * *